United States Patent [19]
Breton et al.

[11] Patent Number: 5,795,574
[45] Date of Patent: Aug. 18, 1998

[54] USE OF AN EXTRACT FROM A NON-PHOTOSYNTHETIC FILAMENTOUS BACTERIUM AND COMPOSITION CONTAINING IT

[75] Inventors: Lionel Breton, Versailles; Lucien Aubert, Cap d'Ail; Jacques Leclaire, Massy; Richard Martin, Rochecorbon; Olivier De Lacharriere, Paris, all of France

[73] Assignee: Société l'Oréal S.A., Paris, France

[21] Appl. No.: 711,109

[22] Filed: Sep. 9, 1996

[30] Foreign Application Priority Data

Sep. 7, 1995 [FR] France ................................. 95 10485
Mar. 27, 1996 [FR] France ................................. 96 03816
Mar. 27, 1996 [FR] France ................................. 96 03818

[51] Int. Cl.$^6$ ................................ A61K 7/06; A61K 7/48; A61K 33/24; A61K 35/78
[52] U.S. Cl. ................ 424/195.1; 424/74; 424/158.1; 424/617; 424/630; 424/639; 424/641; 424/642; 424/646; 424/650; 424/681; 514/15; 514/17; 514/44; 514/183; 514/443; 514/783
[58] Field of Search ................ 424/74, 115, 123, 424/195.1, 282.1, 143.1, 145.1, 146.1, 158.1, 617, 630, 639, 641, 642, 646, 650, 681; 514/783, 2, 12, 15, 17, 21, 44, 183, 443

[56] References Cited

U.S. PATENT DOCUMENTS 5,597,558 1/1997 Aubert et al. ....................... 424/70.1
5,618,521 4/1997 de Rigal et al. ....................... 424/59

FOREIGN PATENT DOCUMENTS 2034687 6/1980 United Kingdom.

*Primary Examiner*—Jeffrey E. Russel
*Attorney, Agent, or Firm*—Burns, Doane, Swecker & Mathis, L.L.P.

[57] ABSTRACT

The present invention relates to the use of at least one extract from at least one non-photosynthetic filamentous bacterium as substance P antagonist in a cosmetic composition or for the preparation of a pharmaceutical composition. The invention also relates to the use of at least one extract from at least one non-photosynthetic filamentous bacterium in a cosmetic composition or for the preparation of a pharmaceutical composition intended for the treatment of disorders associated with an excess in the synthesis and/or in the release of substance P. The invention additionally relates to various compositions containing an extract from at least one non-photosynthetic filamentous bacterium and to a cosmetic treatment process.

77 Claims, No Drawings

USE OF AN EXTRACT FROM A NON-PHOTOSYNTHETIC FILAMENTOUS BACTERIUM AND COMPOSITION CONTAINING IT

BACKGROUND OF THE INVENTION

TECHNICAL FIELD OF THE INVENTION

The present invention relates to the use of at least one extract from at least one non-photosynthetic filamentous bacterium as substance P antagonist in a cosmetic composition or for the preparation of a pharmaceutical composition. The invention also relates to the use of at least one extract from at least one non-photosynthetic filamentous bacterium in a cosmetic composition or for the preparation of a pharmaceutical composition intended for the treatment of disorders is associated with an excess in the synthesis and/or in the release of substance P. The invention relates in addition to various compositions containing an extract from at least one non-photosynthetic filamentous bacterium and to a cosmetic treatment process.

There exist in mammals polypeptides belonging to the family of tachykinins which induce rapid contractions with respect to smooth muscle fibres. Mention may be made, among the compounds of this family, of neurokinin β, neurokinin α and substance P.

Substance P is a polypeptide (undecapeptide) chemical component developed and released by a nerve ending. Localization of substance P is specific to neurones, both in the central nervous system and in the organs at the periphery. Thus, a great many organs or tissues receive neurone afferences containing substance P, in particular the salivary glands, the stomach, the pancreas, the intestines (in the latter, the distribution of substance P is superimposed on Meissner's and Auerbach's intrinsic nerve plexus), the cardiovascular system, the thyroid gland, the skin, the iris and ciliary bodies, the bladder and, very obviously, the peripheral and central nervous systems.

Because of the ubiquitous distribution of substance P, a great many disorders are associated with an excess in the synthesis and/or in the release of substance P.

Substance P is involved in particular in the transmission of pain and in diseases of the central nervous system (for example anxiety, psychoses, neuropathies, neurodegenerative disorders of Alzheimer's senile dementia type, AIDS-related dementia, Parkinson's disease, Down's syndrome, Korsakoff's syndrome, multiple scleroses or schizophrenia), in respiratory diseases (such as, for example, bronchopneumonia) and inflammatory diseases (such as, for example, rheumatoid polyarthritis), in allergic syndromes (such as, for example, asthma, allergic rhinites, allergic pharyngites, urticaria or eczematous dermatites), in gastrointestinal diseases (such as, for example, ulcers, colites or Crohn's disease), in cutaneous disorders (such as, for example, psoriasis, pruriginous diseases, herpes, photodermotoses, atopic dermatites, contact dermatites, lichens, prurigo, pruritus or insect stings), in fibroses and other disorders of maturation of collagens (such as, for example, scleroderma), in cardiovascular disorders, in vasospastic disorders (such as, for example, migraines or Raynaud's disease), in immunological disorders, in disorders of the urinary tract (such as, for example, incontinence or cystitis), in rheumatic diseases, in certain dermatological diseases (such as eczema) and in ophthalmological conditions (such as, for example, conjunctivites, uveitides, ocular pruritus, ocular pains and irritations).

The use of a substance P antagonist is one of the effective therapeutic alternatives in all the conditions mentioned above.

Substance P antagonist is understood to mean any compound capable of partially or indeed completely inhibiting the biological effect of substance P. In particular, for a substance to be recognized as a substance P antagonist, it must induce a coherent pharmacological response (including or not including its binding to the substance P receptor), in particular in one of the following tests:

the antagonist substance must decrease the extravasation of the plasma through the vascular wall induced by capsaicin or by an antidromic nerve stimulation, or alternatively the antagonist substance must cause inhibition of the contraction of the smooth muscles induced by the administration of substance P.

To date, substance P antagonists are used to treat the disorders indicated above. To this end, reference may be made to the documents U.S. Pat. No. 4,472,305, U.S. Pat. No. 4,839,465, EP-A-101929, EP-A-333174, EP-A-336230, EP-A-394989, *, EP-A-498069, EP-A-515681, EP-A-517589, WO-A-92/22569, GB-A-2216529, EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116, EP-A-522808 and WO-A-93/01165.

However, none of these documents envisages or suggests that an extract from at least one non-photosynthetic filamentous bacterium could have a substance P antagonist activity as defined above and could thus be used in particular for treating the disorders indicated above.

The Applicant Company has discovered that an extract from non-photosynthetic filamentous bacteria corresponds to the characteristics defined as characterizing a substance P antagonist and can thus be used as substance P antagonist.

Thus, the invention relates to the use of at least one extract from at least one non-photosynthetic filamentous bacterium as substance P antagonist in a cosmetic composition or for the preparation of a pharmaceutical composition.

The invention also relates to the use of at least one extract from at least one non-photosynthetic filamentous bacterium in a cosmetic composition or for the preparation of a pharmaceutical composition intended for the treatment of disorders associated with an excess in the synthesis and/or in the release of substance P.

Extract from non-photosynthetic filamentous bacteria is understood to mean equally well the supernatant from culturing the said bacteria, the biomass obtained after culturing the said bacteria or alternatively the extracts from the biomass obtained by treatment of this biomass.

The bacterial extracts according to the invention are prepared from non-photosynthetic filamentous bacteria as defined according to the classification of Bergey's Manual of Systematic Bacteriology (vol. 3, sections 22 and 23, 9th edition, 1989), among which may be mentioned the bacteria belonging to the order of the Beggiatoales and more particularly the bacteria belonging to the genera Beggiatoa, Vitreoscilla, Flexithrix or Leucothrix.

The bacteria which have just been defined and of which several have already been described generally have an aquatic habitat and can be found in particular in seawater or in thermal springs. Mention may for example be made, among the bacteria which can be used, of:

*Vitreoscilla filiformis* (ATCC 15551)
*Vitreoscilla beggiatoides* (ATCC 43181)
*Beggiatoa alba* (ATCC 33555)
*Flexithrix dorotheae* (ATCC 23163)
*Leucothrix mucor* (ATCC 25107)
*Sphaerotilus natans* (ATCC 13338)

Use is preferentially made according to the invention of a strain of *Vitreoscilla filiformis*.

In order to prepare the extract according to the invention, the said bacteria can be cultured according to methods known to the person skilled in the art and they can then be separated from the biomass obtained, for example by filtration, centrifuging, coagulation and/or lyophilization. It is possible in particular to prepare the extracts which can be used according to the invention according to the process described by the Applicant Company in Patent Application WO-A-94/02158.

Thus, after culturing, the bacteria are concentrated by centrifuging. The biomass obtained is autoclaved. This biomass can be lyophilized in order to form what is known as the lyophilized extract. Any lyophilization method known to the person skilled in the art can be used to prepare this extract. The supernatant fraction from this biomass can also be filtered in a sterile receptacle in order to remove the suspended particles. The extract is thus obtained which is otherwise known in the text as aqueous extract.

Whatever its form used in the invention, the amount of bacterial extract according to the invention contained in the composition is, of course, a function of the desired effect and can thus vary within wide limits.

To give an order of magnitude in a cosmetic composition, the said bacterial extract is used in an amount representing from 0.0001% to 20% of the total weight of the composition and preferably in an amount representing from 0.001% to 10% of the total weight of the composition.

To give an order of magnitude in a pharmaceutical composition, the said bacterial extract is used in an amount representing from 0.0001% to 30% of the total weight of the composition and preferably in an amount representing from 0.05% to 20% of the total weight of the composition.

Examples of disorders related to an excess in the synthesis and/or in the release of substance P have been seen beforehand in the text.

Thus, according to a particular aspect, a subject of the invention is the use of at least one extract from at least one non-photosynthetic filamentous bacterium in a cosmetic composition or for the preparation of a pharmaceutical composition intended for the treatment of disorders of the central nervous system, respiratory disorders, allergic syndromes, inflammation, pain, gastrointestinal disorders, cutaneous disorders, fibroses, disorders of maturation of collagen, cardiovascular disorders, vasospastic disorders, immunological disorders and disorders of the urinary tract.

In the field of cutaneous disorders, it is known that certain types of skin are more sensitive than others. It is known that there exist, at the cutaneous level, many intolerance phenomena, the symptoms of which are in particular subjective signs which are essentially dysaesthetic sensations. Dysaesthetic sensations is understood to mean more or less painful sensations felt in a cutaneous region, such as smarting, pins and needles, itching or pruritus, burning sensations, warming sensations, discomfort, stabbing pains, and the like.

These phenomena can be the consequence of multiple events, the most commonplace of which will be described as irritation or inflammation but some of which will be due to physiological causes, such as sensitive skins, or indeed even pathological causes, such as, for example, allergy.

However, the symptoms of sensitive skins were, until now, poorly characterized and the problem of these skins was, for this reason, poorly defined; no one knew exactly the process implicated in the sensitivity of the skin. Some thought that a sensitive skin was a skin which reacted to cosmetic products, others that it was a matter of a skin which reacted to a number of external factors, not necessarily related to cosmetic products. Sensitive skins were also classified as allergic skins.

Tests have been developed in order to define sensitive skins, for example tests with lactic acid and with DMSO, which are known to be irritant substances: see, for example, the article by K. Lammintausta et al., Dermatoses, 1988, 36, pages 45–49 and the article by T. Agner and J. Serup, Clinical and Experimental Dermatology, 1989, 14, pages 214–217.

Due to ignorance of the characteristics of sensitive skins, it was, until now, very difficult, indeed impossible, to treat them. In fact, they were treated indirectly, for example by limiting the employment in cosmetic or dermatological compositions of products with an irritant nature, such as surfactants, preservatives or fragrances, as well as the employment of certain cosmetic or dermatological active principles.

After many clinical tests, the Applicant Company has been able to determine the symptoms related to sensitive skins.

The Applicant Company has found that sensitive skins could be divided into two major clinical forms: irritable and/or reactive skins and intolerant skins.

An irritable and/or reactive skin is a skin which reacts by a pruritus, that is to say by itching or by smarting, to different factors, such as the environment, the emotions, food, the wind, friction, shaving, soap, surfactants, hard water with a high calcium concentration, temperature variations or wool. In general, these signs are associated with a dry skin, with or without sores, or with a skin which exhibits an erythema.

An intolerant skin is a skin which reacts with sensations of warming, stabbing pains, pins and needles and/or redness to different factors, such as the environment, the emotions, food and certain cosmetic products. In general, these signs are associated with a hyperseborrhoeic or acneic skin, with or without sores, and with an erythema.

These phenomena may be generalized throughout the body but most of the time they may exhibit well-defined localizations, such as, for example, the scalp, the face, the cutaneous folds, and the like.

"Sensitive" scalps have a less ambiguous clinical symptomatology: the sensations of pruritus and/or of smarting and/or of warming are essentially triggered by local factors such as friction, soap, surfactants, hard water with a high calcium concentration, shampoos or lotions. These sensations are also sometimes triggered by factors such as the environment, the emotions and/or food. An erythema and a hyperseborrhoea of the scalp and a dandruff state are frequently associated with the above signs.

Moreover, in certain anatomical regions, such as the major folds (inguinal, genital, axillary, popliteal, anal, submammary or bend of the elbow regions) and the feet, sensitive skin is reflected by pruriginous sensations and/or dysaesthetic sensations (warming or smarting) related in particular to sweat, to friction, to wool, to surfactants, to certain cosmetic preparations, to hard water with a high calcium concentration and/or to temperature variations.

These combined intolerance phenomena are still related to a conventional inflammatory process and more particularly to an inflammatory reaction of neurogenic type, since it involves the cutaneous nerve fibres.

The Applicant Company has been able to show, in addition, that a sensitive skin was not an allergic skin. In fact, an allergic skin is a skin which reacts to an external agent, an allergen, which triggers an allergic reaction. This relates to an immunological process which only takes place when an allergen is present and which only affects sensitized subjects. On the other hand, the final result of an allergic reaction is also reflected by an acute inflammatory reaction generally associated with an oedema.

In contrast, an essential characteristic of sensitive skin is, according to the Applicant Company, a mechanism of response to external factors which can concern any individual, even if individuals said to have sensitive skins react thereto faster than other individuals. This mechanism is not immunological: it is non-specific.

Whatever the phenomenon envisaged, there exists a stage common to all these mechanisms which is reflected by an inflammatory reaction, the final aspect of which is measured by the release, by the mastocytic cells of the skin, of at least one mediator of the inflammation, such as histamine, serotonin, heparin, leukotrienes, prostaglandins, cytokines, nitrogen monoxide or reactive oxygenated species.

In order to determine if a skin is sensitive or not, the Applicant Company has also developed a test. In fact, after having carried out a great number of tests with the aim of defining a sensitive skin, it has surprisingly found that there existed a connection between people with sensitive skins and those who reacted to a topical application of capsaicin.

The test with capsaicin consists in applying, to approximately 4 cm² of skin, 0.05 ml of a cream comprising 0.075% of capsaicin and in noting the appearance of subjective signs caused by this application, such as smarting, burning sensations and itching. In subjects with sensitive skins, these signs appear between 3 and 20 minutes after application and are followed by the appearance of an erythema which begins at the periphery of the application region.

To date, capsaicin has been used as a medicament, in particular for treating the pain from shingles. Capsaicin causes release of neuropeptides and in particular of tachykinins which arise from nerve endings in the epidermis and in the dermis. The Applicant Company has found that the physiopathologic scheme common to all sensitive skin states was related to a high ability to release tachykinins and more particularly substance P in the skin. The dysaesthetic manifestations which are caused by their release are known as "neurogenic".

No one, until now, had established a connection between substance P and sensitive skin. The clinical signs of sensitive skin are essentially subjective: smarting, pins and needles, pruritus, stabbing pains or warming and they are sometimes associated with erythemas. These signs are due to non-specific external factors. The symptoms appear essentially localized on the face, on the neck and on the scalp but can also appear anywhere on the body.

Thus, the Applicant Company has discovered that one of the essential characteristics of sensitive skins is related to the release of substance P and thus that the use of substance P antagonists can make it possible to obtain a preventive and/or curative effect with respect to sensitive skins.

The Applicant Company has thus envisaged the use of substance P antagonists for the treatment of sensitive skins. Indeed, it has surprisingly found that the incorporation of a substance P antagonist in a composition intended for a topical use makes it possible to prevent irritation and/or dysaesthetic sensations and/or pruritus of the skin.

The invention thus more particularly relates to the use of at least one extract from at least one non-photosynthetic filamentous bacterium in a cosmetic composition or for the preparation of a pharmaceutical composition intended for the treatment of sensitive skins.

A further subject of the present invention is the use of at least one extract from at least one non-photosynthetic filamentous bacterium in a cosmetic composition or for the preparation of a pharmaceutical composition intended to prevent and/or to combat cutaneous irritations and/or sores and/or erythemas and/or warming and/or dysaesthetic sensations and/or pruritus of the skin and/or the mucous membranes.

Advantageously, according to the invention, at least one extract from at least one non-photosynthetic filamentous bacterium can be combined with products with an irritant effect commonly used in the cosmetics or pharmaceutical field, products which are sometimes cosmetic or pharmaceutical active principles. The presence of a substance P antagonist in the form of at least one extract from at least one non-photosynthetic filamentous bacterium in a cosmetic or pharmaceutical composition comprising a product having an irritant effect makes it possible to greatly reduce or indeed eliminate this irritant effect.

This additionally makes it possible to increase the amount of active principle with an irritant effect with respect to the amount of active principle normally used, for the purpose of an improved effectiveness.

Thus, the invention also relates to the use of at least one extract from at least one non-photosynthetic filamentous bacterium in a cosmetic or pharmaceutical composition additionally comprising at least one product with an irritant effect.

The invention also relates to a cosmetic or pharmaceutical composition comprising, in a cosmetically or pharmaceutically acceptable medium, at least one extract from at least one non-photosynthetic filamentous bacterium and, in addition, at least one product with an irritant effect.

Mention may be made, as products with an irritant effect, of, for example, surfactants (ionic or non-ionic), preservatives, organic solvents or active principles, such as α-hydroxy acids (citric, malic, glycolic, tartaric, mandelic or lactic acid), β-hydroxy acids (salicylic acid and its derivatives), α-keto acids, β-keto acids, retinoids (retinol, retinal or retinoic acid), anthralins (dioxyanthranol), anthranoids, peroxides (in particular benzoyl peroxide), minoxidil, lithium salts, antimetabolites, keratolytics, vitamin D and its derivatives, hair dyes or colorants (para-phenylenediamine and its derivatives or aminophenols), perfuming alcoholic solutions (fragrances, toilet waters, aftershaves or deodorants), antiperspirant agents (certain aluminium salts), depilatory or permanent-wave active principles (thiols) or depigmenting active principles (hydroquinone).

The use of substance P antagonist makes it possible in particular to multiply by a factor of 2 to 10 the amount of active principle with an irritant effect with respect to the state of the art, without experiencing any of the discomforts mentioned above. Thus, it is possible to use hydroxy acids up to 50% of the weight of the composition or retinoids up to 5%, while significantly reducing their irritant nature.

In certain cases, the entire mechanism is also under the control of sensitive nerve endings which release neuropeptides, in particular substance P and CGRP.

CGRP, a peptide derived from calcitonin (known under the name Calcitonin Gene Related Peptide or CGRP) is a polypeptide chemical component developed and released by a nerve ending. Localization of CGRP is specific to sensitive nerve fibres (C fibres). Thus, a great many organs or tissues receive neurone afferences containing CGRP: they are in particular the salivary glands, the stomach, the pancreas, the intestines, the cardiovascular system, the thyroid gland and the skin.

Another aim of the present invention is to obtain the broadest possible beneficial effect in the treatment of all these cutaneous conditions and thus to provide a composition which acts on several components of these conditions.

Thus, according to another aspect, a subject of the present invention is the use of at least one extract from at least one non-photosynthetic filamentous bacterium as described above in a cosmetic or pharmaceutical composition additionally comprising at least one extract from cells from at least one plant from the family of the Iridaceae.

According to another aspect, a subject of the present invention is a cosmetic or pharmaceutical composition, characterized in that it comprises, in a cosmetically or pharmaceutically acceptable medium, an extract from at least one non-photosynthetic filamentous bacterium as described above and an extract from plant material from at least one Iridacea.

The extract from at least one Iridacea can be any extract prepared from plant material resulting from the family of the Iridaceae.

The composition can contain an extract from at least one Iridacea obtained from plant material resulting from a whole plant cultivated in vivo or resulting from culturing in vitro.

Thus, for example, according to the invention, the extract can be an extract from a part, indeed from cells from a part, from at least one Iridacea (roots, stem or leaf) or alternatively an extract from undifferentiated cells from at least one Iridacea. Use is preferably made of an extract obtained from undifferentiated cells obtained by cultivating in vivo or culturing in vitro.

The selection pressure imposed by the physicochemical conditions during growth of the plant cells in vitro makes it possible to obtain a standardized plant material which is available throughout the year, in contrast to plants cultivated in vivo.

In vitro culturing is understood to mean all the techniques known to the person skilled in the art which makes it possible artificially to obtain a plant or a part of a plant. It is thus possible to use for example, according to the invention, an extract from roots from at least one Iridacea cultured in vitro or alternatively an extract from undifferentiated cells from at least one Iridacea. Use is preferably made of an extract obtained from plant material cultured in vitro and more preferentially still of an extract obtained from undifferentiated cells cultured in vitro.

Undifferentiated plant cells is understood to mean any plant cell exhibiting none of the features of a specific specialization and capable of living by itself and not in dependence on other cells. These undifferentiated plant cells are optionally capable, under the effect of induction, of any differentiation in accordance with their genome. Depending on the method of culturing chosen, and in particular depending on the culture medium chosen, it is possible to obtain, from the same explant, undifferentiated plant cells exhibiting different features.

The family of the Iridaceae (or Irideae) includes approximately 750 species.

The plants of the family of Iridaceae are especially used for their aromatic and ornamental properties. Mention may be made, among the genera of Iridaceae which can be used according to the invention, of, by way of example, the genera Romulea, Crocus, Iris, Gladiolus, Sisyrinchium or alternatively Hermodactylus.

Mention may be made, as plant material which can be used, of that originating from *Iris germanica, Iris florentina, Iris pallida, Crocus versicolor, Romulea bulbucodium* or alternatively *Gladiolus communis*.

More particularly, according to the invention, use is made of the plant material resulting from the genus Iris and preferentially of the plant material from *Iris pallida*.

Any extraction method known to the person skilled in the art can be used for preparing the extract contained in the composition according to the invention. Mention may in particular be made of alcoholic extracts, in particular ethanolic extracts, or alternatively aqueous/alcoholic extracts.

It is also possible to use an extract prepared by the method described in French Patent Application No. 95-02379 filed by the Applicant Company. Thus, in a first stage, the plant material is milled in a cold aqueous solution, in a second stage the suspended particles are removed from the aqueous solution resulting from the first stage and, in a third stage, the aqueous solution resulting from the second stage is sterilized. This aqueous solution corresponds to the extract.

Moreover, the first stage can advantageously be replaced by a simple freezing operation for the plant tissues (for example at −20° C.), followed by an aqueous extraction resuming the second and third stages described above.

An example of the preparation of an Iridaceae extract which can be used according to the invention is moreover given in the examples.

The amount of extract contained in the composition of the invention is, of course, a function of the desired effect and can thus vary within wide limits.

To give an order of magnitude, if the composition is a cosmetic composition, it can contain an extract from at least one Iridacea in an amount representing from 0.001% to 20% of the total weight of the composition and preferentially in an amount representing from 0.01% to 10% of the total weight of the composition.

To give an order of magnitude, if the composition is a pharmaceutical composition, it can contain an extract from at least one Iridacea in an amount representing from 0.01% to 30% of the total weight of the composition and preferentially in an amount representing from 0.5% to 20% of the total weight of the composition.

According to yet another aspect, a subject of the present invention is the use of an extract from at least one non-photosynthetic filamentous bacterium as described above in a cosmetic or pharmaceutical composition additionally comprising at least one compound which decreases the synthesis, the release and/or the activity of at least one mediator of inflammation, with the exception of steroidal and non-steroidal anti-inflammatory agents.

The invention also relates to a cosmetic or pharmaceutical composition, characterized in that it comprises, in a cosmetically or pharmaceutically acceptable medium, an extract from at least one non-photosynthetic filamentous bacterium as described above and a compound which decreases the synthesis, the release and/or the activity of at least one mediator of inflammation, with the exception of steroidal and non-steroidal anti-inflammatory agents.

Mention may be made, among steroidal anti-inflammatory agents, by way of example, of hydrocortisone, betamethasone valerate or clobetasol propionate.

Non-steroidal anti-inflammatory agents is understood to mean, in this instance, the anti-inflammatory agents as described by Schorderet and Dayer in Pharmacology, "Des concepts fondamentaux aux applications therapeutiques", [Concepts fundamental to therapeutic applications], 1992, chapter 37, pages 541–561, 2nd edition, edited by Frison-Roche/Slatkine. They are arylcarboxylic acids, such as derivatives of salicylic acid or derivatives of anthranilic acid, arylalkanoic acids, such as arylacetic and heteroarylacetic acids or arylpropionic acids, enol acids, such as pyrazolone derivatives or oxicames, and non-acid derivatives, such as, for example, bufexamac (Merck Index, 11th edition (M.I.), 1462), benzydamine (M.I. 1136), epirizole (M.I. 3572), fluproquazone (M.I. 4120) or tiaramide (M.I. 9356).

The composition according to the invention preferentially comprises a compound which decreases the synthesis, the release and/or the activity of at least one mediator of cutaneous inflammation in combination with an extract from at least one non-photosynthetic filamentous bacterium.

The compound which decreases the synthesis, the release and/or the activity of at least one mediator of inflammation is preferably chosen from substance P and/or CGRP antagonists, NO-synthase inhibitors, bradykinin antagonists, cytokine antagonists, histamine antagonists or α-type tumour necrosis factor (TNF-α) antagonists.

Substance P antagonist is understood to mean any compound capable of partially or indeed completely inhibiting the biological effect of substance P. In particular, for a substance to be recognized as a substance P antagonist, it must induce a coherent pharmacological response (including or not including its binding to the substance P receptor), in particular in one of the following tests:

the antagonist substance must decrease the extravasation of the plasma through the vascular wall induced by capsaicin or by an antidromic nerve stimulation, or alternatively the antagonist substance must cause inhibition of the contraction of the smooth muscles induced by the administration of substance P.

For example, according to the invention, it is possible to use one or several substance P antagonists chosen from peptides, non-peptide compounds, such as those comprising at least one heterocycle, nitrogenous compounds comprising at least one benzene ring, salts of monovalent, divalent and trivalent cations, spring waters and their mixtures.

It is possible in the invention to use, for example, sendide and spantide II as peptide substance P antagonists.

Sendide corresponds to the formula:

Tyr-D-Phe-Phe-D-His-Leu-Met-NH$_2$ in which:

Tyr represents tyrosine,
D-Phe represents D-phenylalanine,
Phe represents phenylalanine,
D-His represents D-histidine,
Leu represents leucine,
Met represents methionine.

Spantide II corresponds to the formula:
D-NicLys-Pro-3-Pal-Pro-D-Cl$_2$Phe-Asn-D-Trp-Phe-D-Trp-Leu-Nle-NH$_2$ in which:
D-NicLys represents D-lysine nicotinate,
Pro represents proline,
3-Pal represents 3-pyridylalanine,
D-Cl$_2$Phe represents D-dichlorophenylalanine,
Asn represents asparagine,
D-Trp represents D-tryptophan,
Phe represents phenylalanine,
Leu represents leucine,
Nle represents norleucine.

It is also possible to use in the invention, as peptide subtance P antagonists, the peptides described in the documents U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569 and GB-A-2216529.

The non-peptide substance P antagonists which can be used in the invention are in particular compounds comprising a heteroatom bonded directly or indirectly to a benzene ring or contained in a heterocycle. In particular, this heteroatom is an oxygen, nitrogen or sulphur atom.

Use may in particular be made in the invention, as heterocyclic compound, of those described in the following documents: EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099 or WO-A-93/09116. In particular, the compound comprising at least one nitrogenous heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle or an isoindole derivative.

Mention may be made, as other heterocyclic compounds, of oxygen-containing or sulphur-containing heterocyclic compounds, such as furan derivatives, benzofuran derivatives, thiophene derivatives and benzothiophene derivatives, optionally containing nitrogenous substituents, such as the heterocyclic compounds described in the documents U.S. Pat. No. 4,931,459, U.S. Pat. No. 4,910,317 and EP-A-299457, and more especially alkoxy- and/or aryloxytetrazolylbenzofurancarboxamides or alkoxy- and/or aryloxytetrazolylbenzothiophenecarboxamides.

Mention may be made, as compounds containing a nitrogen atom bonded directly or indirectly to a benzene ring, of those described in the following documents: EP-A-522808 and WO-A-93/01165 and WO-A-93/10073.

The salts of cations which can be used in the invention are in particular the salts of strontium, magnesium, lanthanides with an atomic number ranging from 57 to 71, cobalt, nickel, manganese, barium, yttrium, copper, tin, rubidium, lithium and zinc.

These salts can be, for example, carbonates, salicylates, bicarbonates, sulphates, glycerophosphates, borates, chlorides, nitrates, acetates, hydroxides or persulphates as well as salts of α-hydroxy acids (citrates, tartrates, lactates or malates) or of fruit acids, or alternatively salts of amino acids (aspartate, arginate, glycocholate or fumarate) or salts of fatty acids (palmitate, oleate, caseinate or behenate). The salt is preferably chosen from strontium, manganese, yttrium or magnesium nitrate, strontium, manganese, yttrium or magnesium borate, strontium, manganese or magnesium chloride or magnesium, manganese or strontium sulphate. More preferentially still, theses salts are strontium chloride or strontium nitrate.

Mention may more particularly be made, among the spring waters which can be used according to the invention, of spring waters from the Vichy basin, such as those originating from the springs at Célestins, Chomel, Grande-Grille, Hôpital, Lucas and Parc. Preferentially, according to the invention, water from the spring at Lucas is used.

The substance P antagonists can be used alone or as a mixture.

CGRP antagonist is understood to mean any compound capable of partially or indeed completely inhibiting the biological effect of CGRP. In particular, for a substance to be recognized as a CGRP antagonist, it must induce a coherent pharmacological response (including or not including its binding to the CGRP receptor), in particular in one of the following tests:

the antagonist substance must decrease the vasodilation induced by capsaicin and/or by an antidromic electrical stimulation (applied to an afferent nerve) and/or the antagonist substance must cause inhibition of the release of CGRP by sensitive nerve fibres and/or the antagonist substance must cause inhibition of the contraction of the smooth muscle of the vas deferens induced by CGRP.

Mention may be made, among known CGRP antagonists, of, for example, CGRP 8–37 (sequence of the amino acids 8 to 37 of the N-terminal part of CGRP) or alternatively anti-CGRP antibodies.

The CGRP antagonists can be used alone or as a mixture.

The term NO synthase in fact covers a family of enzymes which, specifically, provide the enzymatic catalysis for L-arginine to citrulline, during which catalysis a gaseous mediator with multiple functions, nitrogen monoxide or NO, is produced. Nitrogen monoxide possesses, because of its structure, an additional electron which makes it extremely reactive chemically. It is well known that such compounds are harmful and a search is underway to limit their production as much as possible. Thus it is that, in the case of nitrogen monoxide, NO-synthase inhibitors have been widely studied.

Thus, according to the invention, NO-synthase inhibitors are products which make it possible in situ in man to partially or indeed completely inhibit the synthesis of nitrogen monoxide (NO).

These are therefore compounds chosen from compounds which inhibit the synthesis and/or which accelerate the catabolism of NO-synthase, compounds which neutralize NO-synthase or compounds which are involved in decreasing the signal transduced by NO-synthase.

Thus, the NO-synthase inhibitor can be chosen from optionally modified, synthetic or natural peptides, synthetic or natural chemical molecules, antisense nucleic acids, ribozymes or anti-NO-synthase antibodies.

Mention may in particular be made, among these NO-synthase inhibitors, of $N^G$-monomethyl-L-arginine (L-NMMA), $N^G$-nitro-L-arginine, the methyl ester of $N^G$-nitro-L-arginine, diphenyleneiodonium chloride, 7-nitroindazole, N(5)-(1-iminoethyl)-L-ornithine, $N^G,N^G$-dimethyl-L-arginine, $N^G,N^G$-dimethyl-arginine, 2-(4-carboxyphenyl)-4,4,5,5-tetramethyl-imidazoline-1-oxy 3-oxide, aminoguanidine, canavanine, ebselen and α-type melanocyte-stimulating hormone.

Use is preferentially made, among NO-synthase inhibitors, of $N^G$-monomethyl-L-arginine and α-type melanocyte-stimulating hormone. NO-synthase inhibitors can be used alone or as a mixture.

Bradykinin is a peptide of plasma origin released from a kininogen precursor by a plasma protease named kallikrein (EC 3.4.21.24). This nanopeptide is one of the key mediators of inflammation and has mitogenic properties. The receptors for this kinin are divided into two main subtypes, B1 and B2. Bradykinin acts in particular on the B2 receptor and causes stimulation of many systems for the production of second messengers, including hydrolysis of inositol phosphates, metabolism of arachidonic acid, phosphorylation of tyrosine residues and depolarization or hyperpolarization of the cell membrane.

The activation of certain receptors causes the activation of phospholipase C and thus the production of inositol 1,4,5-triphosphate (IP3) and of diacylglycerol (DAG). IP3 is known to cause the release of calcium from intracellular storage sites into cells, including keratinocyte cells. Calcium, described as an activator and regulator of many enzymes (proteases or phospholipases), plays an important role in the regulation of the differentiation and of the proliferation of keratinocyte cells.

Bradykinin antagonist is understood to mean any compound capable of partially or indeed completely inhibiting the biological effect of bradykinin.

In particular, for a substance to be recognized as a bradykinin antagonist, it must induce a coherent pharmacological response, including or not including its binding to the bradykinin receptor.

Thus, any compound which can interfere with the effects of bradykinin by the binding thereof to the bradykinin receptor (B1 or B2) and/or any compound which, independently of the binding to the receptor(s), induces, by any mechanism, an effect contrary to that known from bradykinin (for example, interfering with the synthesis of bradykinin) comes within this definition.

Preference is given, among bradykinin antagonists, to the use of compounds which inhibit the synthesis and/or which accelerate the catabolism of bradykinin, compounds which neutralize bradykinin, compounds which block bradykinin receptors, such as those which interfere with the effects of bradykinin by the binding thereof to the bradykinin receptor (B1 or B2), compounds which inhibit the synthesis of bradykinin receptors or compounds which are involved in decreasing the signal transduced by bradykinin. These compounds can be of natural or synthetic origin.

Mention may more particularly be made, among bradykinin antagonists, of optionally modified, synthetic or natural peptides such as D-Arg, [$Hyp^3$, D-$Phe^7$]-bradykinin (NPC567), [$Thi^{5,8}$,D-$Phe^7$]-bradykinin, D-Arg, [$Hyp^3$,$Thi^{5,8}$,D-$Phe^7$]-bradykinin, N-α-adamantaneacetyl-D-Arg, [$Hyp^3$,$Thi^{5,8}$,D-$Phe^7$]-bradykinin or des-$Arg^9$, [$Leu^8$]-bradykinin (all sold by the company Sigma) or alternatively the compounds mentioned in Patents WO 95/08566, WO 95/07294, EP 0623350, EP 0622361, WO 94/11021, EP 0596406, WO 94/06453, WO 94/09001, EP 0578521, EP 0564972, EP 0552106, WO 93/11789, U.S. Pat. No. 5,216, 165, U.S. Pat. No. 5,212,182, WO 92/17201, EP 0496369, EP 0472220, EP 0455133, WO 91/09055, WO 91/02746, EP 0413277, EP 0370453, EP 0359310, WO 90/03980, WO 89/09231, WO 89/09230, WO 89/01780, EP 0334244, EP 0596406, WO 86/07263 or P-guanidobenzoyl-[$Hyp^3$,$Thi^5$, D-$Tic^7$,$Oic^8$]-bradykinin (S 16118) (Feletou M. et al., Pharmacol. Exp. Ther., June 1995, 273, 1078–84), D-Arg, [$Hyp^3$, $Thi^5$,D-$Tic^7$,$Oic^8$]-bradykinin (HOE 140) (Feletou M. et al., Eur. J. Pharmacol., 1995, 274, 57–64), D-Arg, [$Hyp^3$,D-Hype(trans-propyl)$^7$,$Oic^8$]-bradykinin (NPC 17731) (Herzig M. C. S. and Leeb-Lundberg L. M. F., J. Biol. Chem., 1995, 270, 20591–20598) or those mentioned in Bradykinin Antagonists: Development and Applications (Stewart J. M., Biopolymers, 1995, 37, 143–155), or alternatively synthetic or natural chemical molecules, such as, for example, those described in Salvino et al., J. Med. Chem., 1993, 36, 2583–2584.

It is also possible to use, according to the invention, antisense nucleic acids or ribozymes having the purpose of selectively inhibiting the synthesis of bradykinin. These antisense nucleic acids are known to the person skilled in the art. They can act in different ways with respect to DNA or with respect to messenger RNA coding for bradykinin, in particular by blocking binding or progression of the ribosomes along the messenger RNA, by cleaving the messenger RNA with RNase H, or by preventing transportation of messenger RNA from the nucleus to the cytoplasm or alternatively by preventing maturation of the messenger RNA.

It is also possible according to the invention to use anti-bradykinin antibodies or soluble bradykinin receptors, anti-bradykinin receptor antibodies or bradykinin receptor antagonists.

Preferentially, according to the invention, use is made of a compound which interferes with the effects of bradykinin by the binding thereof to the bradykinin receptor (B1 or B2), preferentially to the B2 receptor.

More preferentially still, use is made according to the invention of a bradykinin antagonist chosen from:

D-Arg, [Hyp$^3$,D-Phe$^7$]-bradykinin (NPC567), [Thi$^{5,8}$,D-Phe$^7$]-bradykinin, D-Arg, [Hyp$^3$,Thi$^{5,8}$,D-Phe$^7$]-bradykinin, N-α-adamantaneacetyl-D-Arg, [Hyp$^3$,Thi$^{5,8}$,D-Phe$^7$]-bradykinin, des-Arg$^9$, [Leu$^8$]-bradykinin, P-guanidobenzoyl-[Hyp$^3$,Thi$^5$,D-Tic$^7$,Oic$^8$]-bradykinin (S 16118), D-Arg, [Hyp$^3$,Thi$^5$,D-Tic$^7$,Oic$^8$]-bradykinin (HOE 140), D-Arg, [Hyp$^3$·D-Hype(trans-propyl)$^7$,Oic$^8$]-bradykinin (NPC 17731).

The modified peptide preferentially used according to the invention is D-Arg, [Hyp$^3$,Thi$^5$,D-Tic$^7$,Oic$^8$]-bradykinin (HOE 140).

The bradykinin antagonists can be used alone or as a mixture.

It is known, moreover, that substance P released by sensitive epidermal endings induces a cascade of biochemical events, the first stages of which take place in the mastocytes. Binding of substance P to the mastocytic receptors induces release of many proinflammatory mediators, including histamine or cytokines, such as interleukin-1 (IL1), interleukin-6 (IL6), interleukin-8 (IL8) and α-type tumour necrosis factor (TNF-α).

Histamine, cytokine and/or TNF-α antagonists are understood to mean all compounds capable of inhibiting the release and/or the synthesis and/or the receptor binding of histamine, cytokines and/or TNF-α respectively.

The antagonists which inhibit the receptor binding of histamine are agents specific for the histamine type-1 (H1) receptor.

For a substance to be recognized as a histamine, cytokine or TNF-α receptor antagonist, it must correspond to one of the following characteristics:

have an affinity for the specific receptors for these compounds;

have a histamine, cytokine or TNF-α receptor antagonist pharmacological activity, that is to say induce a coherent pharmacological response in one of the following tests:

for histamine receptor antagonists: inhibition of the contraction of the smooth muscles induced by the administration of histamine;

for cytokine receptor antagonists: inhibition of the adhesion of macrophages induced by cytokines with respect to endothelial cells or inhibition of the release of superoxide anions induced by cytokines with respect to neutrophiles;

for TNF-α receptor antagonists: inhibition of the adhesion of macrophages induced by TNF-α with respect to endothelial cells or inhibition of the release of superoxide anions induced by TNF-α with respect to neutrophiles or inhibition of the mitogenic activity of TNF-α with respect to the fibroblasts of the dermis.

For a substance to be recognized as an antagonist of the release and/or of the synthesis of histamine, of cytokines or of TNF-α, it must correspond to one of the following characteristics:

inhibition of the release of histamine by mastocytes stimulated by the compound 48/80 or stimulated by a calcium ionophore (A23 187)

inhibition of the release of cytokines or of TNF-α by monocytes (U937 cells) differentiated by a phorbol ester (PMA).

The histamine $H_1$-receptor antagonists which can be used in the invention are those conventionally used in treatments for allergic and anaphylactic conditions, as well as those for combating travel sickness. These compounds can be, for example, diethylenediamine derivatives, such as cinnarizine or cyclizine; aminopropane derivatives, such as dexchlorpheniramine or triprolidine; phenothiazine derivatives, such as promethazine or alimemazine; and the compounds mentioned on pages 116 to 118 of the book by Joseph R. Prous, The Year's Drug News, Therapeutic Targets, 1994 edition, Prous Science Publishers, such as cetirizine HCl, ebastine, loratadine or setastine HCl.

The inhibitors of the realease of histamine are in particular oxygen-containing or sulphur-containing heterocyclic compounds such as furan derivatives, benzofuran derivatives, thiophene derivatives and benzothiophene derivatives, optionally containing nitrogenous substituents, such as those described in the documents U.S. Pat. No. 4,931,459, U.S. Pat. No. 4,910,317 and EP-A-299457 and more especially alkoxy- and/or aryloxytetrazolylbenzofurancarboxamides or alkoxy- and/or aryloxytetrazolylbenzothiophenecarboxamides. Mention may be made, by way of example, of 5-methoxy-3-phenoxy-N-(1H-tetrazol-5-yl)benzothiophene-2-carboxamide, 5-methoxy-3-(1-methylethoxy)-N-(1H-tetrazol-5-yl)benzothiophene-2-carboxamide, 6-methoxy-3-(1-methylethoxy)-N-(1H-tetrazol-5-yl)benzothiophene-2-carboxamide, 5-methoxy-3-(1-methylethyl)-N-(1H-tetrazol-5-yl)benzothiophene-2-carboxamide, 3-benzyloxy-5-methoxy-N-(1H-tetrazol-5-yl)benzothiophene-2-carboxamide and 5-methoxy-3-phenoxy-N-(1H-tetrazol-5-yl)benzothiophene-2-carboxamide.

Mention will be made, among cytokine antagonists, of, for example, an antagonist of the release of interleukin-1 which can be used in the invention which can be auranofin or SKF-105809 or alternatively an antagonist of the synthesis of interleukin-1 which can be lactoferrin.

The TNF-α receptor antagonists and the inhibitors of the release and/or of the synthesis of TNF-α which can be used in the invention are in particular lisophyline, A802715 (1-(5-hydroxy-5methyl)hexyl-3-methyl-7-propyl-xanthine) or sulphasalazine.

The histamine, cytokine and TNF-α antagonists can be synthesized or extracted from natural products (plant or animal products).

The histamine, cytokine and TNF-α antagonists can be used according to the invention, separately or in combination, alone or in the form of a mixture.

The amount of compound which decreases the synthesis, the release and/or the activity of at least one mediator of inflammation contained in the composition of the invention is, of course, a function of the desired effect and can therefore vary within wide limits.

To give an order of magnitude, the cosmetic composition of the invention can contain a compound which decreases the synthesis, the release and/or the activity of at least one mediator of inflammation in an amount representing from 0.0001% to 5% of the total weight of the composition and preferentially in an amount representing from 0.001% to 2% of the total weight of the composition.

To give an order of magnitude, the pharmaceutical composition of the invention can contain a compound which decreases the synthesis, the release and/or the activity of at least one mediator of inflammation in an amount representing from 0.0001% to 20% of the total weight of the composition and preferentially in an amount representing from 0.01% to 5% of the total weight of the composition.

Whatever the form of the composition according to the invention, the amount of extract from at least one non-photosynthetic filamentous bacterium contained in the composition according to the invention is, of course, a function of the desired effect. It also depends on the form of the extract used in the composition (aqueous extract, lyophilized extract, and the like). It can therefore vary within wide limits.

To give an order of magnitude, if the composition is a cosmetic composition, it can contain an extract from at least one non-photosynthetic filamentous bacterium in an amount representing from 0.0001% to 5% of the total weight of the composition and preferentially in an amount representing from 0.001% to 1% of the total weight of the composition.

To give an order of magnitude, if the composition is a pharmaceutical composition, it can contain an extract from at least one non-photosynthetic filamentous bacterium in an amount representing from 0.0001% to 10% of the total weight of the composition and preferentially in an amount representing from 0.01% to 5% of the total weight of the composition.

The bacterial extract can be used in a composition which must be ingested, injected or applied on the skin (over any cutaneous region of the body), the hair, the nails or the mucous membranes (buccal, jugal, gingival, genital, anal or conjunctive). Depending on the method of administration, this composition can be provided in all the pharmaceutical dosage forms normally used.

For topical application on the skin, the composition can have the form in particular of an aqueous solution or oily suspension or of a dispersion of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the cream or aqueous or anhydrous gel type, or alternatively of microcapsules or microparticles, or of vesicular dispersions of ionic and/or non-ionic type. These compositions are prepared is according to the usual methods.

They can also be used for the hair in the form of aqueous, alcoholic or aqueous/alcoholic solutions or in the form of creams, gels, emulsions or foams or alternatively in the form of aerosol compositions also comprising a pressurized propellent agent.

For injection, the composition can be provided in the form of an aqueous lotion or of an oily suspension or in the form of a serum. For the eyes, it can be provided in the form of drops and, for ingestion, it can be provided in the form of capsules, of granules, or syrups or of tablets.

The amounts of the different constituents of the compositions according to the invention are those conventionally used in the fields under consideration.

These compositions constitute in particular cleansing, protection, treatment or care creams for the face, for the hands, for the feet, for the large anatomical folds or for the body (for example day creams, night creams, make-up removal creams, foundation creams or anti-sun creams), liquid foundations, make-up removal milks, protective or care body milks, anti-sun milks, lotions, gels or foams for caring for the skin, such as cleansing lotions, anti-sun lotions or artificial tanning lotions, bath compositions, deodorizing compositions comprising a bactericidal agent, aftershave gels or lotions, depilatory creams, compositions for combating insect stings, pain-control compositions or compositions for treating certain diseases of the skin, such as eczema, rosacea, psoriasis, lichens or severe pruritus.

The compositions according to the invention can also comprise solid preparations consisting of cleansing bars or soaps.

The compositions can also be packaged in the form of an aerosol composition also comprising a pressurized propellent agent.

The bacterial extract used according to the invention can also be incorporated in various compositions for hair care and in particular shampoos, hair-setting lotions, treating lotions, styling creams or gels, dye compositions (in particular oxidation dyes), optionally in the form of colour-enhancing shampoos, hair-restructuring lotions, permanent-wave compositions (in particular compositions for the first step of a permanent wave), lotions or gels for combating hair loss, shampoos for combating parasites, and the like.

The compositions can also be for oral use, for example a toothpaste. In this case, the compositions can contain adjuvants and additives usual for compositions for buccal use and in particular surface-active agents, thickening agents, moisturizing agents, polishing agents such as silica, various active ingredients such as fluorides, in particular sodium fluoride, and optionally sweetening agents, such as sodium saccharinate.

When the composition is an emulsion, the proportion of the fatty phase can range from 5% to 80% by weight, and preferably from 5% to 50% by weight, with respect to the total weight of the composition. The oils, the waxes, the emulsifiers and the coemulsifiers used in the composition in the emulsion form are chosen from those conventionally used in the cosmetics field. The emulsifier and the coemulsifier are present, in the composition, in a proportion ranging from 0.3% to 30% by weight, and preferably from 0.5 to 20% by weight, with respect to the total weight of the composition. The emulsion can, in addition, contain lipid vesicles.

When the composition is an oily gel or solution, the fatty phase can represent more than 90% of the total weight of the composition.

In a known way, the cosmetic composition can also contain adjuvants which are usual in the cosmetics field, such as hydrophilic or lipophilic gelling agents, hydrophilic or lipophilic additives, preservatives, antioxidants, solvents, fragrances, fillers, screening agents, odour absorbers and colouring materials. The amounts of these different adjuvants are those conventionally used in the cosmetics field and, for example, from 0.01% to 10% of the total weight of the composition. These adjuvants, depending on their nature, can be introduced in the fatty phase, in the aqueous phase and/or in the lipid spherules.

Mention may be made, as oils or waxes which can be used in the invention, of mineral oils (liquid petrolatum), vegetable oils (liquid fraction of karite butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. Fatty alcohols and fatty acids (stearic acid) can be added to these oils.

Mention may be made, as emulsifiers which can be used in the invention, of, for example, glyceryl stearate, polysorbate 60 and the PEG-6/PEG-32/glycol stearate mixture sold under the name of TEFOSE®63 by the company Gattefosse.

Mention may be made, as solvents which can be used in the invention, of lower alcohols, in particular ethanol and isopropanol, or propylene glycol.

Mention may be made, as hydrophilic gelling agents which can be used in the invention, of carboxyvinyl polymers (carbomer), acrylic copolymers such as acrylate/alkyl acrylate copolymers, is polyacrylamides, polysaccharides such as hydroxypropylcellulose, natural gums and clays and mention may be made, as lipophilic gelling agents, of modified clays such as bentones, metal salts of fatty acids such as aluminium stearates, and hydrophobic silica, ethylcellulose or polyethylene.

The composition can contain other hydrophilic active principles, such as proteins or protein hydrolysates, amino acids, polyols, urea, allantoin, sugars and sugar derivatives, water-soluble vitamins, plant extracts and hydroxy acids.

Use may be made, as lipophilic active principles, of retinol (vitamin A) and its derivatives, tocopherol (vitamin E) and its derivatives, essential fatty acids, ceramides, essential oils or salicylic acid and its derivatives.

According to the invention, it is possible, inter alia, to combine at least one extract from at least one non-photosynthetic filamentous bacterium with other active agents intended in particular for the prevention and/or the treatment of cutaneous conditions.

Mention may be made, among these active agents, of, by way of example:

- agents which modulate cutaneous pigmentation and/or proliferation and/or differentiation, such as retinoic acid and its isomers, retinol and its esters, vitamin D and its derivatives, oestrogens, such as oestradiol, kojic acid or hydroquinone;
- antibacterials, such as clindamycin phosphate, erythromycin or antibiotics from the tetracycline class;
- agents for combating parasites, in particular metronidazole, crotamiton or pyrethroids;
- antifungals, in particular compounds belonging to the imidazole class, such as econazole, ketoconazole or miconazole or their salts, polyene compounds, such as amphotericin B, compounds of the allylamine family, such as terbinafine, or alternatively octopirox;
- antiviral agents, such as acyclovir;
- steroidal anti-inflammatory agents, such as hydrocortisone, betamethasone valerate or clobetasol propionate, or non-steroidal anti-inflammatory agents, such as ibuprofen and its salts, diclofenac and its salts, acetylsalicylic acid, acetaminophen or glycyrrhetinic acid;
- anaesthetic agents, such as lidocaine hydrochloride and its derivatives;
- antipruriginous agents, such as thenaldine, trimeprazine or cyproheptadine;
- keratolytic agents, such as α- and β-hydroxycarboxylic acids or β-ketocarboxylic acids, their salts, amides or esters and more particularly hydroxy acids, such as glycolic acid, lactic acid, salicylic acid, citric acid and generally fruit acids, and 5-(n-octanoyl)salicylic acid;
- agents for combating free radicals, such as α-tocopherol or its esters, superoxide dismutases, certain metal chelating agents or ascorbic acid and its esters;
- antiseborrhoeics, such as progesterone;
- antidandruff agents, such as octopirox or zinc pyrithione;
- antiacne agents, such as retinoic acid or benzoyl peroxide.

Thus, according to a specific embodiment, the invention relates to the use of at least one extract from at least one non-photosynthetic filamentous bacterium in a composition comprising at least one agent chosen from antibacterial agents, agents for combating parasites, antifungal aparasites, anti-viral agents, anti-inflammatory agents, antipruriginous agents, anaesthetic agents, agents for combating free radicals, antiseborrhoeic agents, antidandruff agents, antiacne agents and/or agents which modulate cutaneous pigmentation and/or proliferation and/or differentiation.

An additonal subject of the present invention is a cosmetic treatment process for the purpose of decreasing the irritant effect of a cosmetic composition, characterized in that a composition as described above is applied on the skin, on the hair and/or on the mucous membranes.

The cosmetic treatment process of the invention can be implemented in particular by applying the hygiene or cosmetic compositions as defined above according to the usual technique for the use of these compositions. For example: application of anti-sun compositions or of make-up removal milks, lotions, serums, gels or creams on the skin or on dry hair, application of a hair lotion on wet hair or of shampoos, or alternatively application of a dentifrice on the gums.

The following examples and compositions illustrate the invention without limiting it in any way. In the compositions, the proportions shown are percentages by weight.

EXAMPLE 1

Preparation of an extract from *Vitreoscilla filiformis*

The *Vitreoscilla filiformis* strain (ATCC 15551) is cultured according to the process described in Patent Application WO-A-94/02158. Culturing is carried out at 26° C. for at least 48 hours, until a suitable cell concentration, corresponding to an optical density at 600 nm greater than or equal to 1.5, is obtained. The strain is subcultured at 2% v/v in fresh medium every 48 hours, until a stable culture is obtained. A 1 liter erlenmeyer flask containing 200 ml of fresh medium is then inoculated with 4 ml of the above culture.

Culturing in the erlenmeyer flask is carried out at 26° C. on a culture tray agitated at 100 revolutions/minute. The vessel heel thus obtained is used as inoculum for a 10 l fermenter. Growth is carried out at 26° C., pH 7, 100 revolutions/minute and $PO_2 \geq 15\%$. After 48 hours of growth, the biomass is transferred to a fermenter with a working volume of 600 liters, to be cultured under the same conditions. After 48 h of growth, the cells are harvested. The biomass is then concentrated approximately 50 times by centrifuging.

The concentrate is autoclaved at 121° C. for 40 minutes. After cooling, 2 phases appear. The supernatant liquid phase is then filtered through a 0.22 μm filter in order to remove the particles. This extract can be used as is (aqueous form) or can be lyophilized according to conventional techniques (lyophilized form).

EXAMPLE 2

Measurement of the receptor affinity of the bacterial extract (Example 1, aqueous form) for the human NK1 receptor (human substance P receptor)

A): Receptor affinity

The receptor affinity of the bacterial extract for the human NK1 receptor was measured according to the method described in the article: E. Heuillet et al., J. Neurochem., 60, 1993, 868–876.

The extract is tested at concentrations of 1%, 5% and 10%.

During each experiment, the reference molecule for the receptor studied ([Sar$^9$.Met(O$_2$)$^{11}$]-SP, analogue of substance P described by E. Heuillet (E. Heuillet et al., J. Neurochem., 60, 1993, 868–876)) is tested in parallel at 8 concentrations (n=2), in order to obtain a standard curve allowing the experiment to be validated.

The following are thus obtained: 9% of binding for the extract from Example 1 at 1% 27% of binding for the extract from Example 1 at 5% 91% of binding for the extract from Example 1 at 10%.

The results of this experiment demonstrate an affinity of the bacterial extract in the aqueous form for the human substance P receptor from a concentration of 1%.

The affinity curve traced from the results obtained shows 50% displacement of the natural ligand (IC$_{50}$) by the bacterial extract at a concentration of 6.7%.

B): In vitro functional test

An in vitro functional test, carried out on the human NK1 receptors (human substance P receptors) present on the smooth muscles of the isolated intestine (ileum), is carried out in order to demonstrate the substance P antagonist nature of the bacterial extract.

The in vitro experiments are carried out according to the method described by Dion et al. (Life Sciences, 41, 1987, 2269–2278) and Patacchini et al. (Eur. J. Pharmacol., 215, 1992, 93–98).

After insertion in experimental vessels, the tissues (smooth muscles) are subjected to an initial tension of 1 g. An equilibration period of at least 60 minutes, during which the physiological solution is replaced several times and the initial tension readjusted, is then observed before addition of the extract.

The experiments are carried out in the continuous presence of atropine ($3\times10^{-6}$M), pyrilamine ($3\times10^{-6}$M) and indomethacin ($10^{-6}$M), in order to eliminate the indirect effects of mediators involved during the stimulation of other receptor types present on this tissue.

Each preparation is initially stimulated by a substance P agonist: [Sar$^9$.Met(O$_2$)$^{11}$]-SP, at a concentration of $10^{-8}$M, in order to obtain a "control" contractile response, and the physiological solution is then entirely replaced.

This operation is then repeated every 40 minutes in the presence of increasing concentrations of the bacterial extract, each of them being added 30 minutes before the [Sar$^9$.Met(O$_2$)$^{11}$]-SP.

Inhibition of the activity of the [Sar$^9$.Met (O$_2$)$^{11}$]-SP by 50% is obtained at an extract concentration of 5%.

C): In vivo functional test

An in vivo functional test is carried out with respect to a neurogenic inflammation model in order to demonstrate the substance P antagonist nature of the bacterial extract.

The in vivo experiments are carried out according to the method described by X. J. Xu and coworkers (Neurosciences, 1991, 42, 731–737).

The test consists in causing a neurogenic inflammation by the antidromic stimulation of the saphenous nerve in the anaesthetized animal. This nerve innervates the cutaneous regions of the hind paws. The stimulation causes the release from the nerve endings of substance P, which is partially responsible for the neurogenic inflammation.

The neurogenic inflammation is quantified by measuring the tissular permeability with Evans blue, a marker for the tissular extravasation of plasma albumin which takes place during inflammation.

This reference model is used in the in vivo search for substance P antagonists.

The bacterial extract in its aqueous form, administered at a dilution of 1 in 100, causes a statistically significant decrease of 51% in the neurogenic inflammation.

Conclusions

The bacterial extract exhibits an affinity for the substance P receptor and exerts a substance P antagonist activity.

EXAMPLE 3

Evaluation of the soothing effect of a *Vitreoscilla filiformis* extract

A): Protocol

1) Selection of the subjects 25 subjects with sensitive skins were selected by a dermatologist according to the criteria of the test with lactic acid (K. Lammintausta et al., Dermatoses, 1988, 36, pages 45–49; T. Agner and J. Serup, Clinical and Experimental Dermatology, 1989, 14, pages 214–217). The subjects chosen are subjects exhibiting reactivity and subjects exhibiting strong reactivity.

2) Progression of the test

A complete treatment is carried out with each subject. This treatment is carried out twice daily and successively comprises:

a cleansing stage carried out according to the normal practice of the subject using
  a cleansing cream (formula A) in the case of the use of water for cleansing the skin;
  a cleansing milk (formula B) when cleansing without water;

the use of a care lotion (formula C) applied after cleansing on a perfectly dry skin;

the use of a care cream (formula D) applied after the lotion.

The test took place over a period of 4 weeks with monitoring of the reactivity of the skin:

before the first application of the products, T1 after treatment for 7 days, T8 after treatment for 2 weeks, T15 after treatment for 4 weeks, T29

Monitoring is carried out according to the following procedure:

Application is carried out under single-blind conditions.

Application to a nasogenial furrow of a cotton pad impregnated with 0.1 ml of a 10% aqueous lactic acid solution. This cotton pad is passed 10 times in succession into the nasogenial furrow, application to the nasogenial furrow on the other side of a cotton pad impregnated with 0.1 ml of physiological serum. This cotton pad is passed 10 times in succession into the nasogenial furrow, evaluation of the sensation of smarting with respect to each nasogenial furrow by the subject himself during the first 30 seconds, at 2 minutes and at 5 minutes, a grade being attributed according to the following scale:

0=no smarting

1=slight smarting

2=moderate smarting

3=severe smarting.

The score is drawn up from the difference in the sums of the total scores (30 sec., 2 and 5 min) for each furrow between the side treated with lactic acid and the other side treated with physiological serum, i.e.:

Score=(sum of lactic acid scores)−(sum of physiological serum scores).

B): Compositions used for the test (Formula A): Cleansing cream

Extract from Example 1 (in its lyophilized form) 0.05

Cetyl alcohol 2.00

Glyceryl stearate 2.00

Stearic acid 2.00

Polyglyceryl-3 hydroxylauryl ether 5.00

Mineral oil, pharmaceutical grade 12.00

Carbomer 0.35

Sodium hydroxide 0.15

Fragrance q.s.p.

Methylparaben 0.20

Sterile demineralized water q.s. for 100.00

(Formula B): Cleansing milk

Extract from Example 1 (in its lyophilized form) 0.05

Carbomer 0.40

Sodium hydroxide 0.10

Mineral oil, pharmaceutical grade 5.00

Glyceryl stearate 1.00

Cetyl alcohol 0.50

PEG 100 stearate 0.80

Methylparaben 0.20

Fragrance q.s.p.

Sterile demineralized water q.s. for 100.00

(Formula C): Care lotion

Extract from Example 1 (in its lyophilized form) 0.05

Glycerol 2.00

Methylparaben 0.15

Fragrance q.s.p.

Sterile demineralized water q.s. for 100.00

(Formula D): Care cream

Extract from Example 1 (in its lyophilized form) 0.05

Glyceryl stearate 1.00

PEG 100 stearate 1.00

Stearic acid 1.00

Cetyl alcohol 2.00

Soya oil 3.00

Palm oil 2.00

Cyclomethicone 2.00

Dimethicone 1.00

Polyacrylamide 0.20

Glycerol 3.00

Methylparaben 0.20

Fragrance q.s.p.

Sterile demineralized water q.s. for 100.00

C): Results (in arbitrary units)

| Subject No. | T1 | T8 | T15 | T29 |
|---|---|---|---|---|
| 1 | 2 | 8 | 5 | — |
| 2 | 6 | 1 | 2 | 1 |
| 3 | 8 | 2 | 5 | 3 |
| 4 | 8 | 4 | 2 | 5 |
| 5 | 3 | 4 | 3 | 1 |
| 6 | 8 | np | np | 1 |
| 7 | 5 | 4 | 0 | 2 |
| 8 | 5 | 6 | 6 | 8 |
| 9 | 8 | 4 | 1 | 0 |
| 10 | 6 | 2 | -2 | 2 |
| 11 | 4 | 4 | 3 | 5 |
| 12 | 3 | 3 | 1 | 3 |
| 13 | 5 | 0 | 1 | 4 |
| 14 | 4 | 0 | 0 | 0 |
| 15 | 2 | 2 | 1 | 2 |
| 16 | 2 | 1 | 1 | 2 |
| 17 | 2 | 0 | 3 | -1 |
| 18 | 3 | 4 | 3 | -2 |
| 19 | 7 | 0 | 0 | 3 |
| 20 | 6 | 5 | 3 | 2 |
| 21 | 6 | 4 | 3 | 4 |
| 22 | 3 | 6 | 2 | 3 |
| 23 | 3 | 0 | 0 | -1 |
| 24 | 6 | 1 | 5 | 2 |
| 25 | 6 | 1 | 0 | 3 |
| Total | 121 | 66 | 48 | 52 |
| Mean | 4.84 | 2.75 | 2.00 | 2.17 |
| Standard deviation | 2.14 | 2.29 | 1.91 | 2.29 |
| % Change | | −43.2 | −58.7 | −55.2 | np = not provided.

From the first week of treatment, a very large decrease in cutaneous sensitivity is observed, which decrease continues until the conclusion of the treatment.

EXAMPLE 4

Preparation of an extract from *Iris pallida*

Undifferenciated *Iris pallida* cells, cultured in vitro under axenic conditions, are recovered after culturing in an Erlenmeyer flask or in a fermenter by filtration through a 50 µm sieve. 27.5 ml of demineralized water are added to 55 g of fresh material thus obtained. The whole mixture is milled (Potter, UltraTurrax, and the like) using a Turrax at 24000 rev/min for 1 minute at 4° C. (ice bath). The milled material is centrifuged 15 to 10000 G at 4° C. The supernatant is filtered through a 0.22 µm filter (sterilizing filtration). The extract thus prepared is stored at 4° C. It contains approximately 15 g of dry matter per liter. If the plant material is from the whole plant, the fresh material to be treated is reduced as a function of the dry weight in order to be placed under the same extraction conditions as for the in vitro. The different parts of the plant are removed as a function of the relative weight of each part of the latter. Cold treatment makes it possible to freeze the enzymatic activities and the sterilizing filtration prevents degradation of the active principles by environmental microorganisms. Finally, the vehicle, water, is compatible with the receptors ex vivo and facilitates the cosmetic or pharmaceutical formulations.

EXAMPLE 5

Examples of formulations illustrating the invention and particularly the compositions according to the invention combining at least one extract from at least one non-photosynthetic filamentous bacterium and a product with an irritant effect. These compositions were obtained by simple mixing of the different components.

Composition 1

Make-up removal lotion for the face

Extract from Example 1 (in its lyophilized form) 0.01

Antioxidant 0.05

Isopropanol 40.00

Preservative 0.30

Water q.s. for 100%

Composition 2
  Gel for caring for the face
  Extract from Example 1 (in its lyophilized form) 0.05
  Hydroxypropylcellulose (KLUCEL® H, sold by the company Hercules) 1.00
  Antioxidant 0.05
  Isopropanol 40.00
  Preservative 0.30
  Water q.s. for 100%
Composition 3
  Cream for caring for the face (oil-in-water emulsion)
  Extract from Example 1 (in its aqueous form) 2.00
  Glyceryl stearate 2.00
  Polysorbate 60 (TWEEN® 60, sold by the company ICI) 1.00
  Stearic acid 1.40
  Triethanolamine 0.70
  Carbomer 0.40
  Liquid fraction from karite butter 12.00
  Perhydrosqualene 12.00
  Antioxidant 0.05
  Fragrance 0.50
  Preservative 0.30
  Water q.s. for 100%
Composition 4
  Shampoo
  Extract from Example 1 (in its aqueous form) 1.00
  Hydroxypropylcellulose (KLUCEL® H, sold by the company Hercules) 1.00
  Fragrance 0.50
  Preservative 0.30
  Water q.s. for 100%
Composition 5
  Antiwrinkle care cream for the face (oil/water emulsion)
  Extract from Example 1 (in its lyophilized form) 0.05
  Glyceryl stearate 2.00
  Polysorbate 60 (TWEEN® 60, sold by the company ICI) 1.00
  Stearic acid 1.40
  5-(n-Octanoyl)salicylic acid 0.50
  Triethanolamine 0.70
  Carbomer 0.40
  Liquid fraction from karite butter 12.00
  Perhydrosqualene 12.00
  Antioxidant 0.05
  Fragrance 0.50
  Preservative 0.30
  Water q.s. for 100%
Composition 6
  Pain-control gel
  Extract from Example 1 (in its lyophilized form) 0.03
  Hydroxypropylcellulose (KLUCEL® H, sold by the company Hercules) 1.00
  Antioxidant 0.05
  Lidocaine hydrochloride 2.00
  Isopropanol 40.00
  Preservative 0.30
  Water q.s. for 100%
Composition 7
  Cream for caring for sunburn (oil-in-water emulsion)
  Extract from Example 1 (in its aqueous form) 0.75
  Glyceryl stearate 2.00
  Polysorbate 60 (TWEEN® 60, sold by the company ICI) 1.00
  Stearic acid 1.40
  Glycyrrhetinic acid 2.00
  Triethanolamine 0.70
  Carbomer 0.40
  Liquid fraction from karite butter 12.00
  Sunflower oil 10.00
  Antioxidant 0.05
  Fragrance 0.50
  Preservative 0.30
  Water q.s. for 100%
Composition 8
  Gel for the treatment of acne
  Extract from Example 1 (in its aqueous form) 0.50
  All-trans-retinoic acid 0.05
  Hydroxypropylcellulose (KLUCEL® H) 1.00
  Antioxidant 0.05
  Isopropanol 40.00
  Preservative 0.30
  Water q.s. for 100%
Composition 9
  Lotion for removing the scars due to acne
  Extract from Example 1 (in its lyophilized form) 0.025
  Glycolic acid 50.00
  Hydroxypropylcellulose (KLUCEL® H) 0.05
  NaOH q.s. for pH=2.80
  Ethanol q.s. for 100%
  Preservative 0.30
Composition 10
  Gel for caring for the face
  Extract from Example 1 10.00
  Extract from Example 4 0.50
  Hydroxypropylcellulose (KLUCEL® H, sold by the company Hercules) 1.00
  Antioxidant 0.05
  Isopropanol 40.00
  Preservative 0.30
  Water q.s. for 100%
Composition 11
  Make-up removal lotion for the face
  Extract from Example 1 5.00
  Extract from Example 4 0.10
  Isopropanol 40.00
  Preservative 0.30
  Water q.s. for 100%
Composition 12
  Care cream for the face (oil-in-water emulsion)
  Extract from Example 1 7.00
  Extract from Example 4 1.00
  Glyceryl stearate 2.00
  Polysorbate 60 (TWEEN® 60, sold by the company ICI) 1.00
  Stearic acid 1.40
  Triethanolamine 0.70
  Carbomer 0.40

Liquid fraction from karite butter 12.00
Perhydrosqualene 12.00
Antioxidant 0.05
Preservative 0.30
Water q.s. for 100%

Composition 13
Shampoo
Extract from Example 1 2.00
Extract from Example 4 0.50
Hydroxypropylcellulose (KLUCEL® H, sold by the company Hercules) 1.00
Fragrance 0.50
Preservative 0.30
Water q.s. for 100%

Composition 14
Lotion for removing the scars due to acne
Extract from Example 1 8.00
Extract from Example 4 1.00
Glycolic acid 50.00
Hydroxypropylcellulose (KLUCEL® H, sold by the company Hercules) 0.05
NaOH q.s. for pH=2.8
Ethanol q.s. for 100%
Preservative 0.30

Composition 15
Gel for the treatment of acne
Extract from Example 1 8.00
Extract from Example 4 1.00
All-trans-retinoic acid 0.05
Hydroxypropylcellulose (KLUCEL® H, sold by the company Hercules 1.00
Antioxidant 0.05
Isopropanol 40.00
Preservative 0.30
Water q.s. for 100%

Composition 16
Pain-control gel
Extract from Example 1 0.50
Extract from Example 4 10.00
Hydroxypropylcellulose (KLUCEL® H, sold by the company Hercules) 1.00
Antioxidant 0.05
Lidocaine hydrochloride 2.00
Isopropanol 40.00
Preservative 0.30
Water q.s. for 100%

Composition 17
Cream for caring for sunburn (oil-in-water emulsion)
Extract from Example 1 5.00
Extract from Example 4 1.00
Glyceryl stearate 2.00
Polysorbate 60 (TWEEN® 60, sold by the company ICI) 1.00
Stearic acid 1.40
Glycyrrhetinic acid 2.00
Triethanolamine 0.70
Carbomer 0.40
Liquid fraction from karite butter 12.00
Sunflower oil 10.00
Antioxidant 0.05
Fragrance 0.50
Preservative 0.30
Water q.s. for 100%

Composition 18
Antiwrinkle care cream for the face (oil/water emulsion)
Extract from Example 1 1.00
Extract from Example 4 8.00
Glyceryl stearate 2.00
Polysorbate 60 (TWEEN® 60, sold by the company ICI) 1.00
Stearic acid 1.40
5-(n-octanoyl)salicylic acid 0.50
Triethanolamine 0.70
Carbomer 0.40
Liquid fraction from karite butter 12.00
Perhydrosqualene 12.00
Antioxidant 0.05
Fragrance 0.50
Preservative 0.30
Water q.s. for 100%

Composition 19
Make-up removal lotion for the face
Extract from Example 1 1.00
Strontium chloride 5.00
Antioxidant 0.05
Isopropanol 40.00
Preservative 0.30
Water q.s. for 100%

Composition 20
Gel for caring for the face
Extract from Example 1 0.50
Vichy spring water 10.00
Hydroxypropylcellulose (KLUCEL® H, sold by the company Hercules) 1.00
Antioxidant 0.05
Isopropanol 40.00
Preservative 0.30
Water q.s. for 100%

Composition 21
Care cream for the face (oil-in-water emulsion)
Extract from Example 1 1.00
Auranofin 0.10
Glyceryl stearate 2.00
Polysorbate 60 (TWEEN® 60, sold by the company ICI) 1.00
Stearic acid 1.40
Triethanolamine 0.70
Carbomer 0.40
Liquid fraction from karite butter 12.00
Perhydrosqualene 12.00
Antioxidant 0.05
Preservative 0.30
Water q.s. for 100%

Composition 22
Shampoo
Extract from Example 1 0.50
Strontium chloride 5.00
Hydroxypropylcellulose (KLUCEL® H, sold by the company Hercules) 1.00

Preservative 0.30
Water q.s. for 100%

Composition 23
Lotion for removing the scars due to acne
Extract from Example 1 1.00
HOE 140 0.05
Glycolic acid 50.00
Hydroxypropylcellulose (KLUCEL® H, sold by the company Hercules) 0.05
NaOH q.s. for pH=2.8
Ethanol q.s. for 100%
Preservative 0.30

Composition 24
Gel for the treatment of acne
Extract from Example 1 2.00
CGRP 8–37 0.50
All-trans-retinoic acid 0.05
Hydroxypropylcellulose (KLUCEL® H, sold by the company Hercules) 1.00
Antioxidant 0.05
Isopropanol 40.00
Preservative 0.30
Water q.s. for 100%

Composition 25
Pain-control gel
Extract from Example 1 0.50
Spantide II 0.05
Hydroxypropylcellulose (KLUCEL H, sold by the company Hercules) 1.00
Antioxidant 0.05
Lidocaine hydrochloride 2.00
Isopropanol 40.00
Preservative 0.30
Water q.s. for 100%

Composition 26
Cream for caring for sunburn (oil-in-water emulsion)
Extract from Example 1 1.00
Vichy spring water 10.00
Glyceryl stearate 2.00
Polysorbate 60 (TWEEN® 60, sold by the company ICI) 1.00
Stearic acid 1.40
Glycyrrhetinic acid 2.00
Triethanolamine 0.70
Carbomer 0.40
Liquid fraction from karite butter 12.00
Sunflower oil 10.00
Antioxidant 0.05
Fragrance 0.50
Preservative 0.30
Water q.s. for 100%

Composition 27
Antiwrinkle care cream for the face (oil/water emulsion)
Extract from Example 1 1.00
Lactoferrin 1.00
Glyceryl stearate 2.00
Polysorbate 60 (TWEEN® 60, sold by the company ICI) 1.00
Stearic acid 1.40

5-(n-octanoyl)salicylic acid 0.50
Triethanolamine 0.70
Carbomer 0.40
Liquid fraction from karite butter 12.00
Perhydrosqualene 12.00
Antioxidant 0.05
Fragrance 0.50
Preservative 0.30
Water q.s. for 100%

What is claimed is:

1. A method of cosmetic or pharmaceutical treatment or prevention which comprises administering to a subject in need of admistration of a substance P antagonist a pharmaceutical or cosmetic composition comprising an effective amount of at least one extract from at least one non-photosynthetic filamentous bacterium which is a substance P antagonist contained in a cosmetically or pharmaceutically acceptable carrier.

2. A method of cosmetic or pharmaceutical treatment or prevention of a disorder associated with an excess in the synthesis and/or release of substance P comprising administering to a host in need of substance P antagonist administration an effective amount of a cosmetic or pharmaceutical composition comprising at least one extract from at least one non-photosynthetic filamentous bacterium which is a substance P antagonist contained in a cosmetically or pharmaceutically acceptable carrier.

3. The method according to claim 1 or 2, which is used to treat a disorder selected from the group consisting of disorders of the central nervous system, respiratory disorders, allergic syndromes, inflammation, pain, gastrointestinal disorders, cutaneous disorders, fibroses, disorders of maturation of collagen, cardiovascular disorders, vasospastic disorders, immunological disorders and disorders of the urinary tract.

4. The method according to claim 1 or 2, which comprises the treatment of sensitive skins.

5. The method according to claim 1 or 2, which comprises the prevention or treatment of cutaneous irritations and/or sores and/or erythemas and/or dysaesthetic sensations and/or warming sensations and/or pruritus of the skin and/or the mucous membranes.

6. The method according to claim 1 or 2, wherein said bacterium belongs to the order Beggiatoales.

7. The method according to claim 1 or 2, wherein said bacterium belongs to the genus Beggiatoa, Vitreoscilla, Flexithrix or Leucothrix.

8. The method according to claim 1 or 2, wherein said bacterium is a *Vitreoscilla filiformis* strain.

9. The method of claim 1 or 2, wherein said bacterial extract is contained in an amount representing from 0.0001% to 20% of the total weight of the administered composition.

10. The method of claim 1 or 2, wherein said bacterial extract is contained in an amount representing from 0.0001% to 30% of the total weight of the administered composition.

11. The method according to claim 1 or 2, wherein the administered cosmetic or pharmaceutical composition additionally comprises at least one irritant product.

12. The method according to claim 1 or 2, wherein the administered cosmetic or pharmaceutical composition additionally comprises at least one extract from cells from at least one Iridaceae plant.

13. The method according to claim 1 or 2, wherein the administered cosmetic or pharmaceutical composition additionally comprises at least one compound which decreases the synthesis, the release and/or the activity of at least one mediator of inflammation.

14. A cosmetic or pharmaceutical composition which comprises, in a cosmetically or pharmaceutically acceptable medium, an extract from *Vitreoscilla filiformis* and at least one irritant product.

15. A composition according to claim 14, wherein the irritant product is selected from the group consisting of ionic and non-ionic surfactants, preservatives, organic solvents, α-hydroxy acids, β-hydroxy acids, α-keto acids, β-keto acids, retinoids, anthralins, anthranoids, peroxides, minoxidil, lithium salts, antimetabolites, keratolytics, vitamin D, hair dyes or colorants, perfuming alcoholic solutions, antiperspirant agents, depilatory active principles, permanentwave active principles and depigmenting active agents.

16. A cosmetic or pharmaceutical composition which comprises, in a cosmetically or pharmaceutically acceptable medium, an extract from at least one non-photosynthetic filamentous bacterium and an extract from cells from at least one plant from the family Iridaceae.

17. A composition according to claim 16, wherein the extract obtained from cells from at least one Iridaceae plant is an extract obtained from cells from the whole plant cultivated in vivo.

18. A composition according to claim 16, wherein the extract from cells from at least one Iridaceae plant is an extract from plant material cultured by in vitro.

19. A composition according to claim 16, wherein the cells are undifferentiated cells.

20. A composition according to claim 16, wherein said Iridaceae extract is derived from an Iridaceae genus selected from the group consisting of Romulea, Crocus, Iris, Gladiolus, Sisyrinchium and Hermodactylus.

21. A composition according to claim 16, wherein said Iridaceae extract is an extract derived from Iris.

22. A composition according to claim 16, wherein said Iridaceae extract is derived from *Iris pallida*.

23. A cosmetic composition according to claim 16, wherein said Iridaceae extract is contained in an amount ranging from 0.001% to 20% of the total weight of the composition.

24. A pharmaceutical composition according to claim 16, wherein said Iridaceae extract is contained in an amount ranging from 0.01% to 30% of the total weight of the composition.

25. A cosmetic or pharmaceutical composition which comprises, in a cosmetically or pharmaceutically acceptable medium, an extract from a *Vitreoscilla filiformis* bacterium and a compound which exhibits at least one activity selected from the group consisting of decreasing the synthesis, the release or the activity of at least one mediator of inflammation.

26. A composition according to claim 25, wherein said compound which decreases the synthesis, the release or the activity of at least one mediator of inflammation is a compound which decreases the synthesis, the release or the activity of at least one mediator of cutaneous inflammation.

27. A composition according to claim 25, wherein the compound which decreases the synthesis, the release or the activity of at least one mediator of inflammation is selected from the group consisting of substance P antagonists, CGRP antagonists, NO-synthase inhibitors, bradykinin antagonists, cytokine antagonists, histamine antagonists and α-type tumor necrosis factor (TNF-α) antagonists.

28. A composition according to claim 27, wherein said antagonists are receptor antagonists.

29. A composition according to claim 27 or 28, wherein the substance P antagonist is a substance which results in a decrease in extravasation of plasma through a vascular wall induced by capsaicin, or by an antidromic nerve stimulation or is a substance which results in inhibition of contraction of smooth muscles induced by administration of substance P.

30. A composition according to claim 27, wherein the substance P antagonist is selected from the group consisting of peptides, compounds comprising at least one heterocycle, nitrogenous compounds comprising at least one benzene ring, salts of monovalent, divalent and trivalent cations, spring waters and mixtures thereof.

31. A composition according to claim 30, wherein the peptide is sendide or spantide II.

32. A composition according to claim 30, wherein the compound comprising at least one heterocycle is a nitrogen-containing, oxygen-containing or sulphur-containing heterocyclic compound selected from the group consisting of 2-tricyclyl-2-aminoethane compounds, spirolactam compounds, quinuclidine compounds, azacyclic compounds, aminopyrrolidine compounds, piperidine compounds, aminoazaheterocycles, isoindole compounds, furan compounds, benzofuran compounds, thiophene compounds, and benzothiophene compounds.

33. A composition according to claim 30, wherein the salt is selected from the group consisting of chlorides, acetates, carbonates, bicarbonates, salicylates, borates, nitrates, hydroxides, sulphates, persulphates, glycerophosphates, α-hydroxy acid salts, fruit acid salts, amino acid salts and fatty acid salts of strontium, magnesium, lanthanides with an atomic number ranging from 57 to 71, cobalt, nickel, manganese, barium, yttrium, copper, tin, rubidium, lithium and zinc.

34. A composition according to claim 33, wherein the salt is a strontium salt.

35. A composition according to claim 33, wherein the salt is strontium chloride or strontium nitrate.

36. A composition according to claim 30, wherein the spring water is a water originating from a spring from the Vichy basin.

37. A composition according to claim 36, wherein the spring water originates from the springs at Célestins, Chomel, Grande-Grille, Hôpital, Lucas or Parc.

38. A composition according to claim 36, wherein the spring water originates from the spring at Lucas.

39. A composition according to claim 27, wherein the CGRP antagonist is selected from the group consisting of substances providing a decrease in vasodilation induced by capsaicin or by an antidromic electrical stimulation substances that inhibit release of CGRP by sensitive nerve fibers, and substances which elicit inhibition of contraction of smooth muscle of vas deferens induced by CGRP.

40. A composition according to claim 39, wherein the CGRP antagonist is selected from the group consisting of CGRP 8–37 (sequence of the amino acids 8 to 37 of the N-terminal part of CGRP) and anti-CGRP antibodies.

41. A composition according to claim 27, wherein the NO-synthase inhibitor is a substance which inhibits the synthesis of nitrogen monoxide (NO) upon in vivo administration.

42. A composition according to claim 41, wherein the NO-synthase inhibitor is selected from the group consisting of compounds which inhibit synthesis and/or which accelerate catabolism of NO-synthase, compounds which neutralize NO-synthase, and compounds which are involved in decreasing a signal transduced by NO-synthase.

43. A composition according to claim 41, wherein the NO-synthase inhibitor is selected from the group consisting of modified or unmodified, synthetic or natural peptides; antisense nucleic acids, ribozymes and anti-NO-synthase antibodies.

44. A composition according to claim 41, wherein the NO-synthase inhibitor is selected from the group consisting of $N^G$-monomethyl-L-arginine (L-NMMA), $N^G$-nitro-L-arginine, the methyl ester of $N^G$-nitro-L-arginine, diphenyleneiodonium chloride, 7-nitroindazole, N(5)-(1-iminoethyl)-L-ornithine, $N^G,N^G$-dimethyl-L-arginine, $N^G,N^G$-dimethylarginine, 2-(4-carboxyphenyl)-4,4,5,5-tetramethylimidazoline-1-oxy 3-oxide, aminoguanidine, canavanine, ebselen and α-type melanocyte-stimulating hormone.

45. A composition according to claim 41, wherein the NO-synthase inhibitor is $N^G$-monomethyl-L-arginine or α-type melanocyte-stimulating hormone.

46. A composition according to claim 27, wherein the bradykinin antagonist is selected from the group consisting of compounds which inhibit synthesis and/or which accelerate catabolism of bradykinin, compounds which neutralize bradykinin, compounds which block bradykinin receptors, compounds which inhibit synthesis of bradykinin receptors and compounds which are involved in decreasing signal transduced by bradykinin.

47. A composition according to claim 46, wherein the bradykinin antagonist is selected from the group consisting of modified or unmodified, synthetic or natural peptides; antisense nucleic acids, ribozymes, anti-bradykinin antibodies, soluble bradykinin receptors, anti-bradykinin receptor antibodies and bradykinin receptor antagonists.

48. A composition according to claim 46, wherein the bradykinin antagonist is selected from the group consisting of compounds which interfere with the effects of bradykinin by the binding thereof to a bradykinin receptor.

49. A composition according to claim 46, wherein the bradykinin antagonist is selected from the group consisting of D-Arg, [Hyp$^3$,D-Phe$^7$]-bradykinin (NPC567), [Thi$^{5,8}$,D-Phe$^7$]-bradykinin, D-Arg, [Hyp$^3$,Thi$^{5,8}$,D-Phe$^7$]-bradykinin, N-α-adamantane-acetyl-D-Arg, [Hyp$^3$,Thi$^{5,8}$,D-Phe$^7$]-bradykinin, des-Arg$^9$, [Leu$^8$]-bradykinin, P-guanidobenzoyl-[Hyp$^3$,Thi$^5$,D-Tic$^7$,Oic$^8$]-bradykinin (S 16118), D-Arg, [Hyp$^3$,Thi$^5$,D-Tic$^7$,Oic$^8$]-bradykinin (HOE 140) and D-Arg, [Hyp$^3$,D-Hype(trans-propyl)$^7$,Oic$^8$]-bradykinin (NPC 17731).

50. A composition according to claim 27, wherein the bradykinin antagonist is D-Arg, [Hyp$^3$,Thi$^5$,D-Tic$^7$,Oic$^8$]-bradykinin (HOE 140).

51. A composition according to claim 27, wherein the histamine, cytokine and TNF-α antagonist is a substance selected from the group consisting of histamine, cytokine or TNF-α receptor antagonists and substances that antagonize the release and/or the synthesis of histamine, cytokines or TNF-α.

52. A composition according to claim 51, wherein the substance selected from the group consisting of histamine, a cytokine and TNF-α receptor antagonists is a substance having a selective affinity for receptors for histamines, a cytokine or TNF-α or is a substance which inhibits histamine-induced contraction of smooth muscles, or is a substance that inhibits cytokine-induced adhesion of macrophages to endothelial cells, or is a substance that inhibits cytokine-induced release of superoxide anions by neutrophils, or is a substance that inhibits TNF-α-induced adhesion of macrophages to endothelial cells, or is a substance that inhibits TNF-α-induced release of superoxide anions by neutrophils, or is a substance that inhibits TNF-α-induced mitogenic activity of dermal fibroblasts.

53. A composition according to claim 51, wherein the histamine receptor antagonist is selected from the group consisting of diethylenediamine compounds, aminopropane compounds, phenothiazine compounds, cetirizine HCl, ebastine, loratadine and setastine HCl.

54. A composition according to claim 51, wherein the antagonist of the release of histamine is selected from the group consisting of oxygen-containing or sulphur-containing heterocyclic compounds.

55. A composition according to claim 51, wherein the inhibitor of the release of histamine is selected from the group consisting of 5-methoxy-3-phenoxy-N-(1H-tetrazol-5-yl)benzothiophene-2-carboxamide, 5-methoxy-3-(1-methylethoxy)-N-(1H-tetrazol-5-yl)benzothiophene-2-carboxamide, 6-methoxy-3-(1-methylethoxy)-N-(1H-tetrazol-5-yl)benzothiophene-2-carboxamide, 5-methoxy-3-(1-methylethyl)-N-(1H-tetrazol-5-yl)benzothiophene-2-carboxamide, 3-benzyloxy-5-methoxy-N-(1H-tetrazol-5-yl) benzothiophene-2-carboxamide and 5-methoxy-3-phenoxy-N-(1H-tetrazol-5-yl)benzothiophene-2-carboxamide.

56. A composition according to claim 27, wherein the cytokine antagonist is selected from the group consisting of antagonists of the release of interleukin-1, and antagonists of the synthesis of interleukin-1.

57. A composition according to claim 51, wherein said TNF-α receptor antagonist and said inhibitor of the release and/or of the synthesis of TNF-α are selected from the group consisting of lisophyline, (1-(5-hydroxy-5methyl)hexyl-3-methyl-7-propyl-xanthine) and sulphasalazine.

58. A cosmetic composition according to claim 25, wherein the compound which decreases the synthesis, the release and/or the activity of at least one mediator of inflammation is contained in an amount ranging from 0.0001% to 5% of the total weight of the composition.

59. A pharmaceutical composition according to claim 25, wherein the compound which decreases the synthesis, the release and/or the activity of at least one mediator of inflammation is contained in an amount ranging from 0.0001% to 20% of the total weight of the composition.

60. A composition according to claim 14 or 16, which is suitable for the treatment of a disorder selected from the group consisting of disorders of the central nervous system, respiratory disorders, allergic syndromes, inflammation, pain, gastrointestinal disorders, cutaneous disorders, fibroses, disorders of maturation of collagen, cardiovascular disorders, vasospastic disorders, immunological disorders and disorders of the urinary tract.

61. A composition according to claim 14 or 16, which is suitable for treating or preventing cutaneous irritations and/or sores and/or erythemas and/or dysaesthetic sensations and/or warming sensations and/or pruritus of the skin and/or mucous membranes.

62. A composition according to claim 14 or 16, which further comprises an agent selected from the group consisting of antibacterial agents, agents for combating parasites, antifungal agents, antiviral agents, anti-inflammatory agents, antipruriginous agents, anaesthetic agents, agents for combating free radicals, antiseborrhoeic agents, antidandruff agents, antiacne agents and agents which decrease at least one of cutaneous pigmentation, proliferation and differentiation.

63. A composition according to claim 16, wherein said bacterium belongs to the order Beggiatoales.

64. A composition according to claim 16, wherein said bacterium belongs to the genus Beggiatoa, Vitreoscilla, Flexithrix or Leucothrix.

65. A composition according to claim 16, wherein said bacterium is a *Vitreoscilla filiformis* strain.

66. A cosmetic composition according to claim 16, wherein said bacterial extract is contained in an amount ranging from 0.0001% to 5% of the total weight of the composition.

67. A pharmaceutical composition according to claim 16, wherein said bacterial extract is contained in an amount ranging from 0.0001% to 10% of the total weight of the composition.

68. A method of cosmetic treatment which comprises topically applying to a subject in need of such treatment a composition according to claim 14 to the skin, the hair or the mucous membranes.

69. A method of cosmetic treatment which comprises topically applying to a subject in need of such treatment a composition according to claim 16 to the skin, hair or the mucous membranes.

70. A method of cosmetic treatment which comprises topically applying to a subject in need of such treatment a composition according to claim 15 to the skin, hair or the mucous membranes.

71. The composition according to claim 32, wherein said compound is a tetrazolylbenzofurancarboxamide or a tetrazolylbenzothiophenecarboxamide.

72. The composition according to claim 46, wherein said bradykinin antagonist inhibits the binding of bradykinin to the B1 or B2 receptor.

73. The composition of claim 48, wherein said bradykinin receptor is B1 or B2.

74. The composition of claim 23, wherein the total weight of said Iridaceae extract ranges from 0.01% to 10% relative to the total weight of said composition.

75. The composition of claim 24, wherein the total weight of said Iridaceae extract ranges from 0.5% to 20% relative to the total weight of the composition.

76. The method of claim 9, wherein said amount ranges from 0.001% to 10% relative to the total weight of the composition.

77. The method of claim 10, wherein said amount ranges from 0.05% to 20% relative to the total weight of the composition.

* * * * *

UNITED STATES PATENT AND TRADEMARK OFFICE
CERTIFICATE OF CORRECTION

PATENT NO. : 5,795,574
DATED : August 18, 1998
INVENTOR(S) : Lionel BRETON et al.

It is certified that error appears in the above-identified patent and that said Letters Patent is hereby corrected as shown below:

Column 2, line 15, change "cause inhibition" to --reduce inhibition--.

Signed and Sealed this

Seventeenth Day of October, 2000

Attest:

Q. TODD DICKINSON

Attesting Officer      Director of Patents and Trademarks